United States Patent [19]

Ono et al.

[11] 4,440,620

[45] Apr. 3, 1984

[54] MEASURING ELECTRODE DEVICE

[75] Inventors: Noriaki Ono; Takashi Kamiyama, both of Tokyo, Japan

[73] Assignee: Olympus Optical Co., Ltd., Tokyo, Japan

[21] Appl. No.: 449,700

[22] Filed: Dec. 14, 1982

[30] Foreign Application Priority Data

Dec. 22, 1981 [JP] Japan .................. 56-206100
Dec. 22, 1981 [JP] Japan .................. 56-206101
Dec. 22, 1981 [JP] Japan .................. 56-206103

[51] Int. Cl.³ .................. G01N 27/30; G01N 27/46
[52] U.S. Cl. .................. 204/403; 204/415;
204/419; 324/438; 128/635
[58] Field of Search .............. 204/1 E, 1 K, 403, 415,
204/416, 419, 433; 128/635, 632; 324/438

[56] References Cited

U.S. PATENT DOCUMENTS

| | | | |
|---|---|---|---|
| 2,913,386 | 11/1959 | Clark | 204/415 |
| 3,357,908 | 12/1967 | Riseman et al. | 204/415 |
| 3,539,455 | 11/1970 | Clark | 204/1 E |
| 3,718,563 | 2/1973 | Krull et al. | 204/415 |
| 3,756,923 | 9/1973 | Dahms | 204/415 X |
| 4,062,750 | 12/1977 | Butler | 204/415 |
| 4,073,713 | 2/1978 | Newman | 204/403 |
| 4,119,498 | 10/1978 | Edwall et al. | 204/415 X |
| 4,297,173 | 10/1981 | Hikuma et al. | 204/403 X |

*Primary Examiner*—G. L. Kaplan
*Assistant Examiner*—Nam X. Nguyen
*Attorney, Agent, or Firm*—Frishauf, Holtz, Goodman & Woodward

[57] ABSTRACT

A measuring electrode device comprises a pH electrode arranged within an outer casing and having a pH sensitive member in contact with an electrolyte housed in the outer casing. The electrolyte reacts with a predetermined gas in a liquid to be inspected and varies its pH. The pH sensitive member includes a semiconductor substrate and a pH sensitive membrane formed on the substrate and in contact with the electrolyte. The pH sensitive membrane is formed of at least one element selected from the group consisting of silicon nitride, aluminum oxide and tantalum pentoxide. A potential difference is produced between the pH sensitive membrane and the electrolyte in accordance with the variation of the pH of the electrolyte. Thus, a potential difference is produced between the pH electrode and a reference electrode according to the variation of the pH of the electrolyte.

20 Claims, 6 Drawing Figures

MEASURING ELECTRODE DEVICE

BACKGROUND OF THE INVENTION

The present invention relates to a measuring electrode device for measuring the concentration of gas or biochemical substance dissolved in a liquid to be inspected.

A method for measuring the concentration of carbon dioxide gas dissolved in blood (partial pressure of carbon dioxide gas) for example, is known as one means for inspecting the metabolic functions of a living body. A carbon dioxide gas measuring electrode is generally used to measure this concentration. Heretofore, a Severinghaus type electrode has been used as the electrode of this type, and this electrode is described in detail in "A Symposium of pH and Blood Gas Measurement," p 126 to 142 issued by J. & A. Churchill Ltd., in 1959. In FIG. 1, the Severinghaus type carbon dioxide gas measuring electrode is shown.

The carbon dioxide gas measuring electrode 100 has an outer casing 102, a gas permeable film 106, a gas permeable membrane 106 mounted via an O-ring 104 at the lower end of the outer casing 102 and closing the lower end of the casing 102, an external electrolyte 108 which is housed in the casing 102, and a pH electrode 110 and a reference electrode 112 which are arranged in the casing 102 and are dipped in the electrolyte 108. The membrane 106 allows gas dissolved in the liquid to be inspected to permeate through the membrane 106, but does not allow the water or ions in the liquid to permeate through the membrane 106. The electrolyte 108 is, for example, a dilute solution of sodium bicarbonate. It reacts with carbon dioxide in the gas coming through the membrane 106 and its pH is varied. The reference electrode 112 which is dipped in the electrolyte 108 employs a Ag/AgCl electrode. To keep the potential of the electrode 112 constant, the electrolyte 108 contains a predetermined quantity of a chloride such as sodium chloride (NaCl). The electrode 112 is a silver wire which is formed in a wire shape, and is chlorided or silvered by an electrolysis of the electrode in a hydrogen chloride (HCl) solution. Even if the pH of the electrolyte 108 is altered, the potential of the reference electrode 112 will not vary.

The pH electrode 110 has an inner casing 114, a known pH sensitive glass membrane 116 extending to the lower end of the casing 114, an internal electrolyte 118 which is housed in the casing 114 to maintain an electric contact with the membrane 116 and consists of a liquid having a predetermined pH such as, for example, phosphoric acid buffer solution, and an internal electrode 120 which is arranged in the casing 114 to maintain electric contact with the electrolyte 118 and is composed of Ag/AgCl electrode. The glass 116 of the electrode 110 and the membrane 106 are disposed to confront each other through a hydrophilic spacer 122 such as cellophane. The electrolyte 108 permeates the spacer 122 to form an external electrolyte layer 124.

When the membrane 106 of the carbon dioxide gas measuring electrode 100 is dipped in a liquid to be inspected, such as blood, the membrane 106 allows only the gas dissolved in the liquid to permeate through the membrane to the side of the electrolyte layer 124 but does not allow the liquid or ions to permeate through the membrane. The carbon dioxide gas in the permeating gas is reacted with water in the layer 124 and reaches an equilibrium state as designated by following formula:

$$CO_2 + H_2 \rightleftarrows H_2CO_3 \rightleftarrows H^+ + HCO_3^-$$

$H+$ ions produced by this reaction alter the pH of the electrolyte layer 124. The glass membrane 116 senses the variation in the pH, and a potential difference responsive to the pH is produced in the boundary between the membrane 116 and the layer 124. This potential difference is transmitted through the electrolyte 118 to the electrode 120, and a potential difference responsive to the variation in the pH of the external electrolyte is produced between the electrode 120 and the reference 112. Then, the potential difference is measured by an external potential detector, and the concentration of the carbon dioxide gas in the liquid can be obtained indirectly from the measured result.

The conventional carbon dioxide gas measuring electrode 100 employs the pH sensitive glass film 116 as the pH electrode 110 for detecting the variation in the pH of the external electrolyte 108. Accordingly, the measuring electrode has a disadvantage in that the electrode 100 becomes large, resulting in the need for a large amount of liquid to be inspected (such as blood) in order to perform the measuring operation. This disadvantage can be improved to some degree by making the pH sensitive glass membrane of the pH electrode 110 smaller. However, when the glass membrane 116 is reduced in size, its resistance remarkably increases, causing the induction of noise and resulting in a difficulty in making accurate measurements. Further, when the glass membrane 116 is very reduced in thickness, its resistance can be reduced, but since the material is glass, its mechanical strength also decreases, resulting in easy breakage. In addition, since the pH electrode 110 is constructed to store the internal electrolyte 108 therein as described above, the electrode cannot be decreased to more than a certain degree, with the result that the carbon dioxide gas measuring electrode 100 storing the pH electrode should be increased in size.

SUMMARY OF THE INVENTION

The present invention has been made in consideration of this and has for its object to provide a measuring electrode device which can be reduced in size, can maintain, even if the size is reduced, low impedance, will not induce noise, and can provide excellent mechanical strength and good responsiveness.

According to one aspect of the invention, there is provided a measuring electrode device which comprises a pH electrode having a pH sensitive member, which includes a semiconductor substrate and a pH sensitive membrane formed on the substrate. This pH sensitive membrane is thus formed on the semiconductor substrate. Accordingly, even if the membrane is reduced in thickness, sufficient mechanical strength can be obtained. Therefore, the pH sensitive member can be reduced in size, thereby reducing the pH electrode and the entire device. Since the pH sensitive membrane can be reduced in thickness, the impedance of the pH sensitive membrane can be reduced, and noise can be prevented. Thus, the responsiveness of the device can be improved.

DETAILED DESCRIPTION OF THE PREFERRED EMBODIMENT

An embodiment of a measuring electrode device according to the present invention will be described in detail with reference to the accompanying drawings.

Figure 1:
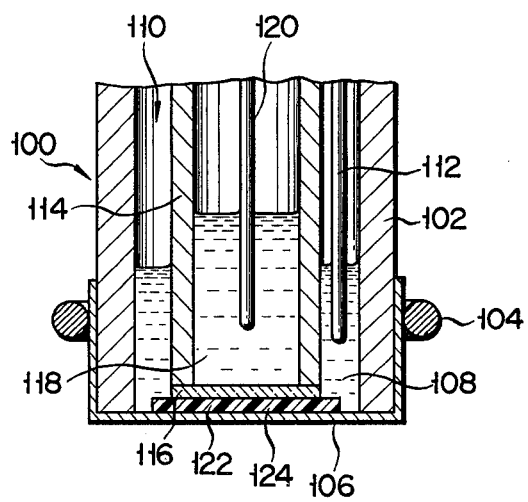
FIG. 1 is a longitudinal sectional view showing the essential part of a conventional measuring electrode device.
Figure 2:
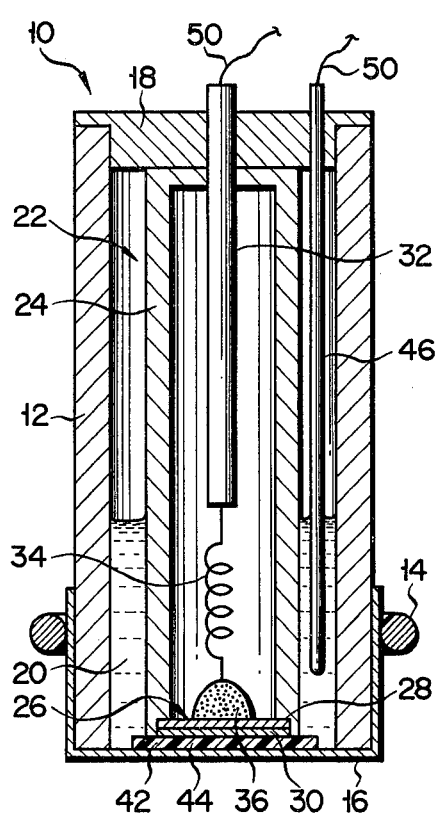
FIG. 2 is a longitudinal sectional view showing a measuring electrode device of an embodiment according to the present invention.

As shown in FIG. 2, a measuring electrode device 10 has a cylindrical outer casing 12 open at both ends. At the lower end of the casing 12 a gas permeable membrane 16 is mounted via an O-ring 14. The lower end opening of the casing 12 is closed by the gas permeable membrane 16. The membrane 16 is formed, for example, of a synthetic resin having gas permeability and a hydrophobic property such as, for example, Teflon resin, silicon resin, etc. When the lower end of the casing 12 is dipped in a liquid to be inspected, the membrane 16 allows only the gas dissolved in the liquid to permeate through the membrane toward the inside of the casing 12 but does not allow water or ions to permeate the membrane. On the other hand, the upper end of the casing 12 is closed by an upper end plate 18 which is detachably attached to the upper end of the casing 12.

An electrolyte 20 is housed in the casing 12 in contact with the membrane 16. In this embodiment, the measuring electrode device 10 is used for measuring a carbon dioxide gas, and the electrolyte 20 is a dilute solution of sodium bicarbonate. The electrolyte 20 reacts with the carbon dioxide in the gas coming through the membrane 12 and has its pH varied.

Further, the electrolyte 20 has a predetermined pH even if the electrolyte 20 is not reacted with the gas. In addition, the electrolyte 20 contains a predetermined concentration of a chloride such as, for example, sodium chloride (NaCl) so as to maintain the potential of a reference electrode which will be described later.

Figure 3:
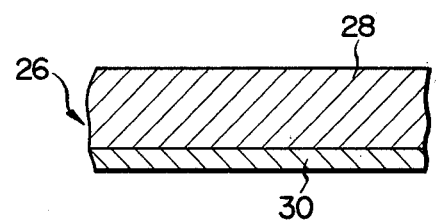
FIG. 3 is a sectional view showing an enlarged pH sensitive member of the device in FIG. 2.

The measuring electrode device 10 further has a pH electrode 22 which is arranged in the casing 12. The pH electrode 22 has a cylindrical inner casing 24 open at the lower end. This inner casing 24 is arranged coaxially with the casing 12, and is dipped at the lower end portion in the electrolyte 20. The upper end of the casing 24 is closed. The casing 24 is attached at the upper end to the upper end plate 18. The electrode 22 has a pH sensitive member 26 which is mounted at the lower end of the casing 24 to close the lower end of the casing 24. The member 26, has as shown in FIGS. 2 and 3, a semiconductor substrate such as, for example, a silicon substrate 28, and a pH sensitive membrane 30 formed on the substrate 28. The membrane 30 is formed by a vacuum deposition, sputtering or a CVD (Chemical Vapour Deposition) of at least one of silicon nitride ($Si_3N_4$), aluminum oxide ($Al_2O_3$) and tantalum pentoxide ($Ta_2O_5$) on the silicon substrate 28. The member 26 is mounted on the casing 24 so that the membrane 30 faces at a predetermined space to the membrane 16.

Figure 4:
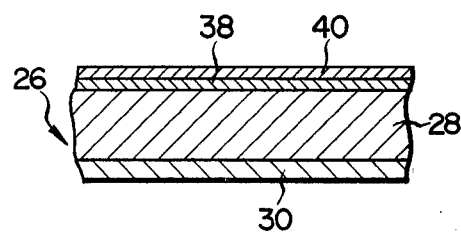
FIG. 4 is a sectional view showing a modified example of the pH sensitive member.

Further, the electrode 22 has a lead wire 32 which extends externally through the casing 24 and the upper end plate 18 from the casing 12. One end of the core wire 34 of the lead wire 32 is connected through a conductive resin (adhesive) 36 to the substrate 28. It is noted that the core wire 34 of the lead wire 32 cannot be soldered directly to the substrate 28. When the core wire 34 will be soldered, an aluminum electrode layer 38 is deposited on the side opposite to the side surface of the substrate 28 on which the membrane 30 is formed as shown in FIG. 4, a chromium-copper (Cr-Cu) electrode layer 40 is further deposited on the layer 38, and the wire 34 is soldered onto the layer 40. The electrode 22 can detect the potential which is produced at the membrane 30 of the member 26.

In the casing 12 a spacer 42 which is formed of a substance having hydrophilic property such as cellophane is interposed between the membrane 16 and the member 26 as required. Part of the electrolyte 20 permeates through the spacer 42, thereby forming an electrolyte layer 44 between the membrane 16 and the membrane 30.

The measuring electrode device 10 further has a reference electrode 46 which is arranged in the casing 12. The electrode 46 is dipped at the lower end in the electrolyte 20, and externally extends at the upper end from the upper end plate 18 of the outer casing 12. This electrode 46 is formed of a silver wire which is formed in a wire shape, and is chlorided and silvered by an electrolysis in a hydrogen chloride (HCl) solution on the surface. The potential of the electrode 46 is, as described above, constant since a chloride such as sodium chloride (NaCl) is contained in a predetermined concentration in the electrolyte 20.

An operation of the measuring electrode device 10 thus constructed will be described.

Figure 5:
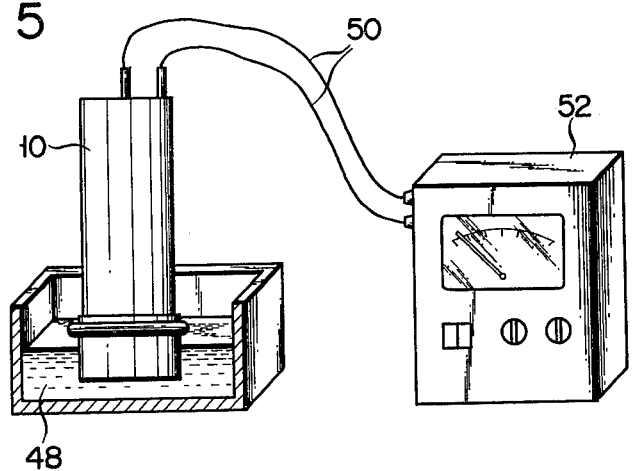
FIG. 5 is a schematic view showing the state of measuring a liquid to be inspected by using the device in FIG. 2.

The case in which the concentration of carbon dioxide in a liquid to be inspected such as blood is measured with the measuring electrode device 10 will now be described. As shown in FIG. 5, the device 10 is set to be dipped at the lower end and hence, the membrane 16 is dipped in blood 48. The electrodes 22 and 46 of the device 10 are respectively connected through lead wires 50 to a potential detector 52. Thus, gases which are contained in the blood 48 permeate the membrane 16 and move to the side of the electrolyte 20. The blood or ions do not permeate the membrane 16. The gas to be permeated is not limited only to the carbon dioxide gas. Other gases, such as oxygen $O_2$, which are dissolved in the blood can permeate through the membrane 16, but the gases other than carbon dioxide gas do not contribute to the following reaction.

The carbon dioxide gas in the blood thus moved to the electrolyte layer 44 reacts with the water in the electrolyte 20 and reaches an equilibrium state as designated by the following formula:

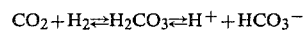

$$CO_2 + H_2O \rightleftharpoons H_2CO_3 \rightleftharpoons H^+ + HCO_3^-$$

The $H^+$ ions which are produced in this reaction alter the pH of the layer 44. The variation in the pH is sensed by the membrane 30 of the member 26, and a potential difference responsive to the variation in the pH is produced in the boundary between the membrane 30 and the layer 44. This potential difference is applied through the substrate 28 and the resin 36 to the core wire 34 of the lead wire 32. In this manner, a potential difference responsive to the pH value in the layer 44 is presented between the core wire 34 and the electrode 46. It is known that the variation in the pH is proportional to log PCO2 from Henderson-Hasselbalch's formula. Accordingly, the above potential difference is amplified and measured by the potential detector 52, and the measured value is calculated by an arithmetic unit (not shown), thereby obtaining the concentration of the carbon dioxide gas in the blood 48.

As described above, the pH sensitive membrane 30 of the member 26 is formed by a vacuum deposition, sputtering or CVD method on the substrate 28, and this membrane 30 can be made extremely thin and uniform. The membrane 30 may be formed about 500 Å to 5000 Å, and preferably about 1000 Å to 1500 Å thick. The reason for limiting the thickness of the membrane 30 is because, when the membrane 30 is formed less than about 500 Å, the thickness becomes irregular or a defect such as pinholes may be produced, with the result that the yield is deteriorated and the durability of the membrane decreases. Further, when the thickness of the membrane 30 exceeds about 5000 Å, the impedance of the membrane 30 increases, causing noise to be readily induced and a sensing velocity to be delayed.

The silicone substrate 28 is widely used in the semiconductor industry, and its surface can be inexpensively mirror-finished by etching to make it smoother. Further, the substrate 28 as a substrate for the membrane 30, can increase the mechanical strength of the membrane 30, and has a function of transmitting the potential difference produced at the boundary between the membrane 30 and the layer 44 to the core wire 34 of the lead wire 32. Therefore, in this case, the silicon substrate 28 may be any of P type and n type conductivity, and may also be either of single crystal or polycrystalline structure. It is necessary for the membrane 30 to be formed extremely thinly and uniformly. Since the substrate 28 can be mirror-polished as described above, the preferable membrane 30 which has no pinholes can be readily formed on the substrate 28. Further, the substrate 28 does not influence the impedance and responsiveness of the membrane 30. Accordingly, the thickness of the silicon substrate 28 can be set to a desired value. Therefore, the mechanical strength of the membrane 30 can be increased by forming a thick substrate 28.

The measuring electrode device 10 thus constructed has the following features and advantages:

The electrode 22 has the pH sensitive member 26, which includes the silicone substrate 28 and the pH sensitive membrane 30 formed on the substrate 28. The membrane 30 is extremely thin, but still has excellent mechanical strength due to the substrate 28. Therefore, the member 26 may be reduced to approx. ¼ the size of the conventional one, resulting in the reduction in the entire measuring electrode device 10. Moreover, the member 26 is connected directly to the lead wire 32. Accordingly, it is not necessary to fill the internal electrolyte in the casing 24, the electrode 22 can be reduced in size, with the result that the entire measuring electrode device can be further reduced in size. In addition, the membrane 30 is thinly formed, and accordingly its impedance is small, resulting in a very little noise production. Therefore, the measuring electrode device 10 has excellent responsiveness.

In the embodiment described above, the measuring electrode device 10 is used to measure the carbon dioxide gas. However, the measuring electrode device of the present invention is not limited to carbon dioxide gas, but can be applied for the measurement of other gases such as ammonia gas.

When the concentration of ammonia gas which is dissolved in the liquid to be inspected is measured by the measuring electrode device 10, a dilute solution of ammonium chloride is used as the electrolyte 20 in FIG. 2. The electrolyte 20 reacts only with the ammonia gas of the gases which permeate the membrane 16, and its pH will vary. The other construction of the measuring electrode device 10 is the same as that of the above embodiment.

The case in which the concentration of ammonia gas in a liquid to be inspected is measured by the measuring electrode device 10 will now be described. As shown in FIG. 5, the measuring electrode device 10 is set to be dipped at the lower end, that is, the membrane 16 is put in the liquid 48 which is to be inspected. The electrodes 22 and 46 of the device 10 are respectively connected through the lead wire 50 to the potential detector 52. Then, the gases which exist in the liquid 48 permeate the membrane 16 and move to the side of the electrolyte 20. The ammonia gas in the gases thus moved to the layer 20 reacts with the water in the layer 20 and reaches an equilibrium states as designated by the following formula:

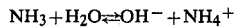

$$NH_3 + H_2O \rightleftarrows OH^- + NH_4^+$$

The $OH^-$ ions thus produced by this reaction alters the pH of the layer 44. This variation in the pH is sensed by the membrane 30 of the member 26, and a potential difference responsive to the variation in the pH is produced in the boundary between the membrane 30 and the layer 44. This potential difference is transmitted through the substrate 28 and the conductive resin 36 to the core wire 34 of the lead wire 32, and the potential difference responsive to the pH value in the layer 44 is presented between the core wire 34 and the electrode 46. Then, the potential difference is amplified and measured by the potential detector 52, and the measured value is calculated by an arithmetic unit (not shown), thereby obtaining the concentration of the ammonia gas in the liquid 48.

Further, the measuring electrode device 10 is not limited to carbon dioxide gas and ammonia gas, but can measure the concentration of a biochemical substance such as urea dissolved in the liquid to be inspected.

In the field of clinical examination, the measurements of nitrogen urea in the blood, hereinafter referred to as "BUN," perform useful functions for the diagnosis of kidney disease, uremia, substantial liver disease, protein catabolism, etc. Further, measurements of BUN are desired to be performed simultaneously with the above items as an emergency examination item together with electrolyte and glucose such as sodium (Na), potassium (K), etc.

Heretofore, analysis of this type generally has employed a wet type chemical method which used an enzyme reagent, but this is a lengthy process and required careful operation. Recently, enzyme solidifying techniques and clinical examination equipment which utilizes the techniques have been developed which have excellent measuring time and operability as compared with the above-described wet type chemical method. A column method which solidifies the BUN decomposing enzyme in a tube, membrane and porous glass bead, and an enzyme electrode method which mounts a solidified enzyme membrane on the surface of an ion selection electrode or a gas electrode are such known methods. The BUN is decomposed by urease of decomposing enzymes into ammonia and dioxidized carbonic acid.

Figure 6:
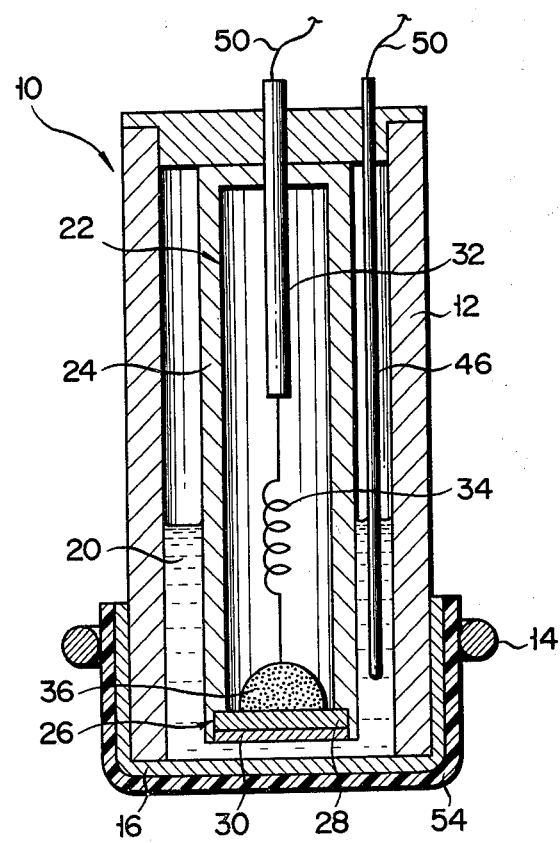
FIG. 6 is a longitudinal sectional view showing a modified embodiment adapted for measuring a biochemical substance with the device in FIG. 2.

FIG. 6 shows a modification applied with the measuring electrode device 10 for measuring the BUN. In this modification, the measuring electrode device 10 has urease solidified enzyme membrane 54 which is mounted on the outside of the gas permeable membrane 16 via an O-ring 14 to cover the gas permeable membrane. This membrane 54 decomposes, when contacting a liquid to be inspected, the BUN existing in the liquid is converted into ammonia and carbonic acid. The electrolyte 20 may be a dilute solution of ammonium chloride which varies its pH upon reaction with the ammonia or a dilute solution of sodium bicarbonate which varies its pH upon reaction with the carbonic acid.

The case in which the concentration of the BUN contained in the liquid to be inspected is measured with the measuring electrode device 10 will now be described. As shown in FIG. 5, the measuring electrode device 10 is disposed to be dipped at the lower end, that is, the urease solidified enzyme membrane 54 is dipped in the blood 48. Then, the electrodes 22 and 46 of the device 10 are respectively connected to the potential detector 52 through the lead wire 50. Thus, the blood 48 is contacted with the urease solidified enzyme membrane 54, and the BUN contained in the blood is decomposed by the urease according to the following formula:

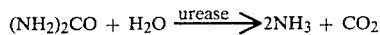

$$(NH_2)_2CO + H_2O \xrightarrow{urease} 2NH_3 + CO_2$$

The ammonia and carbon dioxide gas produced by this reaction are diffused in the atmosphere due to the partial pressure difference from atmospheric pressure, and in this case most of the ammonia and the carbon dioxide gas permeate through the gas permeable membrane 54 and the membrane 16 and move to the side of the electrolyte 20. In the case where the electrolyte 20 is a dilute solution of sodium bicarbonate, only the carbonic acid gas reacts with the water in the electrolyte, and reaches an equilibrium state as designated by the following formula:

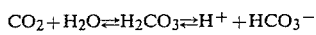

$$CO_2 + H_2O \rightleftharpoons H_2CO_3 \rightleftharpoons H^+ + HCO_3^-$$

In the case where the electrolyte 20 is a dilute solution of ammonium chloride, only the ammonia reacts with the water in the electrolyte, and reaches an equilibrium state as designated by the following formula:

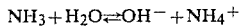

$$NH_3 + H_2O \rightleftharpoons OH^- + NH_4^+$$

The pH of the electrolyte 20 varies in any of the above reactions. The variation in the pH is sensed by the membrane 30 of the member 26, and a potential difference responsive to the variation in the pH is produced in the boundary between the electrolyte 20 and the membrane 30. This potential difference is transmitted through the substrate 28 and the conductive adhesive 36 to the lead wire 32, and the potential difference responsive to the variation in the pH is thus produced between the electrode 22 and the electrode 46. This potential difference is amplified and measured by the potential detector 52, and the measured value is calculated by an arithmetic unit (not shown), thereby obtaining the concentration of the BUN in the blood 48.

As described in detail above, the measuring electrode device 10 has excellent responsiveness, can be reduced in size as compared with the conventional device, and can measure various gases or biochemical substances contained in a liquid to be inspected.

The embodiment described above is for purposes of description and illustration only, and does not limit the present invention. For example, the shapes of the outer and inner casings 12, 14 are not limited to the cylindrical shape, but may also be formed in other shapes such as, for example, square, rectangular or hexagonal shape.

What we claim is:

1. A measuring electrode device for measuring the concentration of a predetermined gas or a biochemical substance dissolved in a liquid to be inspected, comprising:

an outer casing of substantially cylindrical shape having an open one end;

a gas permeable membrane attached to the one end of the outer casing to close the one end and to permeate only gas dissolved in the liquid to be inspected toward the outer casing when contacted with the liquid to be inspected;

an electrolyte housed in the outer casing and in contact with the gas permeable membrane and which varies in the pH upon reaction with the predetermined gas permeated through the gas permeable membrane;

a reference electrode arranged in the outer casing, partly dipped in the electrolyte and maintained at a predetermined potential;

a pH electrode arranged within the outer casing and having a pH sensitive member in contact with the electrolyte, the member having a semiconductor substrate and a pH sensitive membrane formed on the substrate and in contact with the electrolyte, a potential difference being produced between the pH sensitive membrane and the electrolyte according to a variation of the pH of the electrolyte, the pH sensitive membrane being formed of at least one element selected from the group consisting of silicon nitride, aluminum oxide and tantalum pentoxide, and a potential difference being produced between the pH electrode and the reference electrode according to the variation of the pH of the electrolyte.

2. The measuring electrode device according to claim 1, wherein said electrolyte is a dilute solution of sodium bicarbonate which varies its pH upon reaction with carbonic acid.

3. The measuring electrode device according to claim 1, wherein said electrolyte is a dilute solution of ammonium chloride which varies its pH upon reaction with ammonia gas.

4. The measuring electrode device according to claim 1, wherein said pH electrode has an inner casing of substantially cylindrical shape which is arranged in the outer casing and has an opened one end dipped in the electrolyte, and the pH sensitive member is attached to the one end of the inner casing to close the one end thereof and confronts in a predetermined space the gas permeable membrane.

5. The measuring electrode device according to claim 4, wherein said pH electrode has a lead wire extending externally from the inner casing to the outer casing, the lead wire is connected to the semiconductor substrate of the pH sensitive member and transmits the potential difference produced in the boundary between the pH sensitive membrane and the electrolyte through the substrate out of the outer casing.

6. The measuring electrode device according to claim 5, wherein said lead wire is connected via a conductive adhesive to the substrate.

7. The measuring electrode device according to claim 5, wherein said pH sensitive member has an aluminum electrode layer formed on the side opposite to the side formed with the pH sensitive membrane of the substrate and a chromium-copper (Cr-Cu) electrode layer formed on the aluminum electrode layer, and the lead wire is soldered to the chromium-copper electrode layer.

8. The measuring electrode device according to claim 4, wherein said outer and inner casings are respectively formed in cylindrical shape, and the inner casing is arranged coaxially with the outer casing.

9. The measuring electrode device according to claim 1, wherein said reference electrode is formed of a silver wire of wire shape chlorided and silvered on the surface thereof, and has an upper end extending external to the outer casing.

10. The measuring electrode device according to claim 9, wherein said electrolyte contains a predetermined concentration of chloride for maintaining the potential of the reference electrode constant.

11. The measuring electrode device according to claim 1, wherein said semiconductor substrate comprises a silicon substrate.

12. The measuring electrode device according to claim 1, wherein said pH sensitive member is formed to a thickness of substantially 500 A to 5000 A.

13. The measuring electrode device according to claim 1, which further comprises a solidified enzyme membrane mounted on the outside of the gas permeable membrane and covering the gas permeable membrane, the solidified enzyme membrane is formed by a solidifying enzyme for decomposing a predetermined biochemical substance contained in the liquid to be inspected in contact with the liquid to be inspected.

14. The measuring electrode device according to claim 13, wherein said solidified enzyme membrane is formed of urease for decomposing nitrogen ureide contained in the liquid to be inspected into carbon dioxide gas and ammonia upon contacting the liquid to be inspected.

15. The measuring electrode device according to claim 14, wherein said electrolyte is a dilute solution of sodium bicarbonate which varies its pH upon reaction with carbonic acid.

16. The measuring electrode device according to claim 14, wherein said electrolyte is a dilute solution of ammonium chloride which varies its pH upon reaction with ammonia gas.

17. The measuring electrode device according to claim 14, wherein said pH electrode has an inner casing of substantially cylindrical shape which is arranged in the outer casing and has an opened one end dipped in the electrolyte, and the pH sensitive member is attached to the one end of the inner casing to close the one end thereof and confronts in a predetermined space the gas permeable membrane.

18. The measuring electrode device according to claim 17, wherein said pH electrode has a lead wire extending externally form the inner casing to the outer casing, the lead wire is connected to the semiconductor substrate of the pH sensitive member and transmits a potential difference produced in the boundary between the pH sensitive membrane and the electrolyte through the substrate out of the outer casing.

19. The measuring electrode device according to claim 14, wherein said reference electrode comprises a silver wire of wire shape chlorided and silvered on the surface thereof, and has an upper end extending external to the outer casing.

20. The measuring electrode device according to claim 19, wherein said electrolyte contains a predetermined concentration of chloride for maintaining the potential of the reference electrode constant.

* * * * *